US011331122B2

(12) United States Patent
Zeng et al.

(10) Patent No.: US 11,331,122 B2
(45) Date of Patent: May 17, 2022

(54) NEEDLE GUIDE APPARATUS FOR ENDOCAVITY ULTRASOUND INTERVENTION

(71) Applicant: JingFang Precision Medical Device (Shenzhen) Co., Ltd., Guangdong (CN)

(72) Inventors: Junhua Zeng, Guangdong (CN); Jianfeng Zou, Guangdong (CN); Yufu Lan, Guangdong (CN)

(73) Assignee: JingFang Precision Medical Device (Shenzhen) Co., Ltd., Shenzhen (CN)

( * ) Notice: Subject to any disclaimer, the term of this patent is extended or adjusted under 35 U.S.C. 154(b) by 500 days.

(21) Appl. No.: 16/464,292

(22) PCT Filed: Aug. 10, 2018

(86) PCT No.: PCT/CN2018/099795
§ 371 (c)(1),
(2) Date: May 27, 2019

(87) PCT Pub. No.: WO2019/140889
PCT Pub. Date: Jul. 25, 2019

(65) Prior Publication Data
US 2020/0305931 A1 Oct. 1, 2020

(30) Foreign Application Priority Data

Jan. 18, 2018 (CN) .......................... 201820081569.9

(51) Int. Cl.
*A61B 8/12* (2006.01)
*A61B 17/34* (2006.01)
(Continued)

(52) U.S. Cl.
CPC ............ *A61B 17/3478* (2013.01); *A61B 8/12* (2013.01); *A61B 1/0014* (2013.01);
(Continued)

(58) Field of Classification Search
CPC ............ A61B 17/3403; A61B 17/3478; A61B 1/0014; A61B 2017/00274;
(Continued)

(56) References Cited

U.S. PATENT DOCUMENTS 5,873,828 A * 2/1999 Fujio ...................... A61B 8/445
600/439
2005/0203413 A1 9/2005 Fichtinger et al.

FOREIGN PATENT DOCUMENTS

CN 105832414 A 8/2016
CN 106821466 A 6/2017

OTHER PUBLICATIONS

Search report of counterpart European Patent Application No. 18900916.0 dated Jan. 21, 2021.

* cited by examiner

*Primary Examiner* — Mark D Remaly

(57) ABSTRACT

A needle guide apparatus for endocavity ultrasound intervention is provided, comprising a plastic bracket and a needle guiding passage made of metal that is provided in the plastic bracket, wherein the plastic bracket has a mounting structure that is detachably mounted to an endocavity ultrasound probe, and the needle guiding passage comprises a needle insertion groove provided by a metal head and a guiding groove provided by a metal guiding tube, the metal guiding tube is at least partially housed in the plastic bracket, and at least an inlet end of the metal head is exposed outside the plastic bracket. The needle guide apparatus for endocavity ultrasound intervention forms an all-metal needle guiding passage in the plastic bracket, so that the needle can smoothly and cleanly enter the human body during the ultrasonic interventional operation, and the interventional operation is safe, reliable and easy to operate.

7 Claims, 2 Drawing Sheets

(51) Int. Cl.
*A61B 1/00* (2006.01)
*A61B 17/00* (2006.01)

(52) U.S. Cl.
CPC .............. *A61B 2017/00296* (2013.01); *A61B 2017/00477* (2013.01); *A61B 2017/3405* (2013.01); *A61B 2017/3413* (2013.01)

(58) Field of Classification Search
CPC ........... A61B 2017/00296; A61B 2017/00477; A61B 2017/00964; A61B 2017/3405; A61B 2017/3413; A61B 2034/2063; A61B 2090/0801; A61B 2090/378; A61B 8/12; A61B 90/11
See application file for complete search history.

NEEDLE GUIDE APPARATUS FOR ENDOCAVITY ULTRASOUND INTERVENTION

FIELD

The present application generally relates to medical instruments, more particularly to a needle guide apparatus for endocavity ultrasound intervention.

BACKGROUND

At present, clinical applications of interventional diagnosis and treatment with the help of endocavity ultrasound probe are more and more popular. In interventional operation, an endocavity ultrasound probe needs to be equipped with a needle guide apparatus to guide a needle to reach the surgical target position. There are two types of commonly used endocavity needle guide apparatuses: one is a metal needle guide apparatus that can be repeatedly sterilized by using stainless steel, and the other is a disposable plastic needle guide apparatus that is made of plastic material and sterilized at the factory. For the disposable endocavity needle guide apparatus, its guiding channel for guiding the needle is composed of a needle insertion groove and a guiding groove, and there are cases that the needle insertion groove and the guiding groove are both made of plastic material, and also cases that the needle insertion groove is made of plastic material and the guide groove is made of metal material. In both cases, during the process of entering the needle guide apparatus, a sharp needle tip of the needle may be in contact with the plastic needle insertion groove or the plastic guide groove. The needle tip of the needle is easily inserted into the plastic material and the tip is deformed and damaged. The plastic material surface on the needle guide apparatus is cut, and it is possible to remove a part of the plastic debris remaining on the needle, thereby causing plastic debris attached to the needle to enter the human body and causing health hazards.

SUMMARY

The technical problem to be solved by the present application is to provide a needle guide apparatus for endocavity ultrasound intervention that can ensure a smooth and clean entering of a needle into the human body in view of the above-mentioned drawbacks of the prior art.

The technical solution adopted by the present application to solve the technical problem thereof is to provide a needle guide apparatus for endocavity ultrasound intervention, comprising a plastic bracket and a needle guiding passage made of metal that is provided in the plastic bracket, wherein the plastic bracket has a mounting structure that is detachably mounted to an endocavity ultrasound probe, and the needle guiding passage comprises a needle insertion groove provided by a metal head and a guiding groove provided by a metal guiding tube, the metal guiding tube is at least partially housed in the plastic bracket, and at least an inlet end of the metal head is exposed outside the plastic bracket.

In one embodiment, an outlet end of the metal head and an inlet end of the metal guiding tube are positioned by a positioning structure to dock the needle insertion groove with the guiding groove.

In one embodiment, t a positioning groove that is matched with the inlet end of the metal guiding tube is provided at the outlet end of the metal head, and the inlet end of the metal guiding tube is inserted in the positioning groove.

In one embodiment, the metal head and the plastic bracket are provided with a limiting structure that cooperates to restrict the metal head from moving along an axis of the metal guiding tube and rotating around the axis of the metal guiding tube.

In one embodiment, the limiting structure comprises an anti-rotation groove formed on an outer surface of the outlet end of the metal head and an anti-rotation block formed on the plastic bracket at a corresponding position to be filled into the anti-rotation groove.

In one embodiment, the limiting structure further comprises a first limiting slot and a second limiting slot that are formed on opposite sides of the outer surface of the outlet end of the metal head and are oppositely penetrated to the positioning groove, and a first limiting block and a second limiting block that are formed on the plastic bracket at corresponding positions to be filled into the first limiting slot and the second limiting slot respectively.

In one embodiment, the plastic bracket is injection molded integrally on the needle guiding passage.

In one embodiment, the metal guiding tube is a circular tube providing a circular guiding groove, and the needle insertion groove of the metal head has a bellmouth shape or a partial bellmouth shape which is open upward.

In one embodiment, the plastic bracket is provided with a needle outlet that is docked with the needle guiding passage, and an inner surface of the needle outlet is larger than an inner surface of the needle guiding passage.

The needle guide apparatus for endocavity ultrasound intervention according to the present application forms an all-metal needle guiding passage in the plastic bracket, so that the needle can smoothly and cleanly enter the human body during the ultrasonic interventional operation, and the interventional operation is safe, reliable and easy to operate.

BRIEF DESCRIPTION OF THE DRAWINGS

The present application will be further described with reference to the accompanying drawings and embodiments, in which.

DETAILED DESCRIPTION

To explain objects, technical solutions and advantages of the present application more clearly, the present application will be further described with reference to the accompanying drawings and embodiments in the following. It should be understood that, the specific embodiments described here are only for explanation, but not for limitation to the present application.

Figure 1:
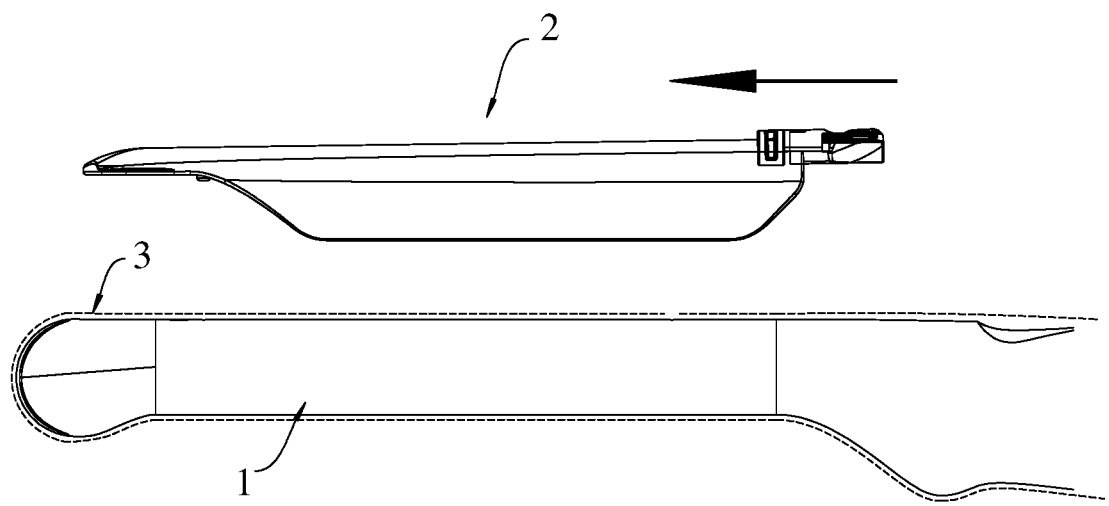
FIG. 1 is a schematic exploded view showing the use of a needle guide apparatus for endocavity ultrasound intervention in combination with an endocavity ultrasound probe according to an embodiment of the present application.
Figure 2:
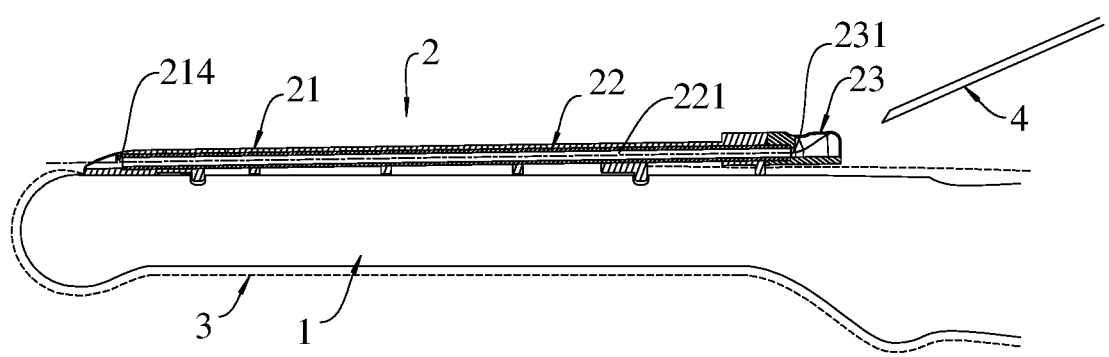
FIG. 2 is a sectional view showing the use of the needle guide apparatus for endocavity ultrasound intervention in combination with the endocavity ultrasound probe as shown in FIG. 1.
Figure 3:
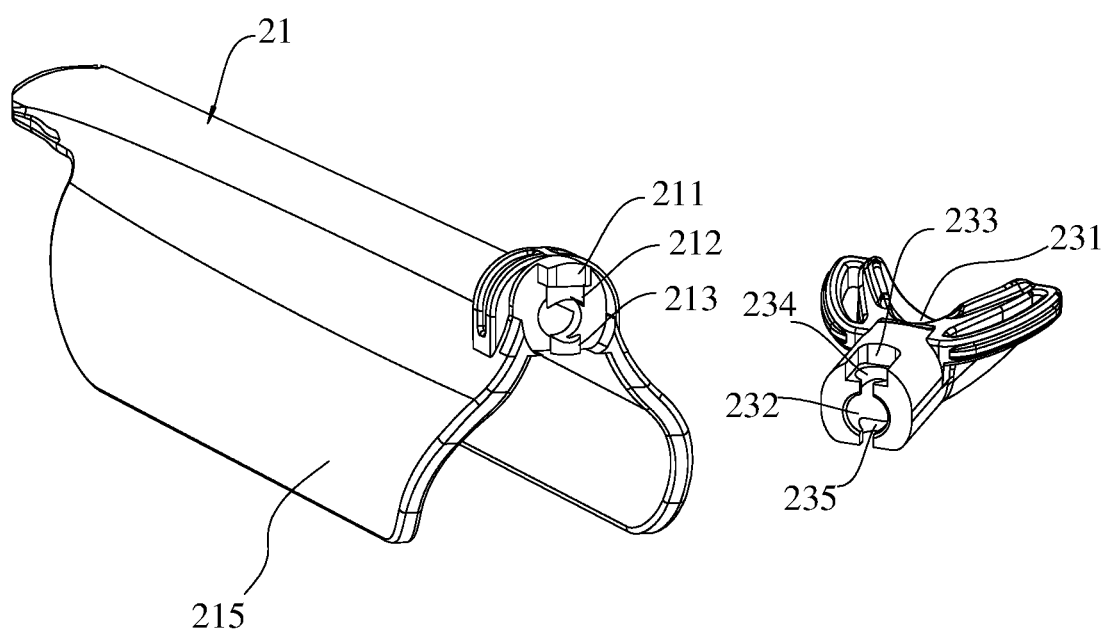
FIG. 3 is a schematic view showing the structure of a plastic bracket in combination with a metal head of the needle guide apparatus for endocavity ultrasound intervention as shown in FIG. 1.

As shown in FIG. 1 to FIG. 3, a needle guide apparatus for endocavity ultrasound intervention 2 according to an embodiment of the present application is mainly composed of a plastic bracket 21, a metal guiding tube 22 and a metal head 23, wherein the metal guiding tube 22 is housed in the plastic bracket 21, and the metal head 23 is exposed outside the plastic bracket 21. The metal guiding tube 22 is preferably a circular tube providing a circular guiding groove 221 extending in a guiding direction of an interventional operation. The metal head 23 provides a needle insertion groove 231 that docks with the guiding groove 221, thereby forming an all-metal needle guiding passage in the plastic bracket 21, guiding a needle 4 to perform an interventional operation, and preventing the needle 4 from coming into contact with the plastic bracket 21.

Referring to FIG. 3, a positioning groove 232 is provided at an outlet end of the metal head 23, and shape of the positioning groove 232 is matched with an inlet end of the metal guiding tube 22. Inserting the inlet end of the metal guiding tube 22 into the positioning groove 232 allows the metal guiding tube 22 to be positioned opposite the metal head 23 to dock the guiding groove 221 with the needle insertion groove 231. After the metal guiding tube 22 and the metal head 23 are positioned, they can be placed in an injection mold mounted on an injection molding machine, and then the plastic bracket 21 is formed thereon by injection molding. After the injection molding is completed, the plastic bracket 21, the metal guiding tube 22, and the metal head 23 form an integral part, that is, the needle guide apparatus for endocavity ultrasound intervention 2. Referring to FIG. 2, after the injection molding is completed, the metal guiding tube 22 is housed in the plastic bracket 21, and the metal head 23 is fixed to the plastic bracket 21 by a limit structure that cooperates with the plastic bracket 21. Specifically, as shown in FIG. 3, an anti-rotation groove 233 is provided on an outer surface of the outlet end of the metal head 23, and an anti-rotation block 211 is formed at a corresponding position on the plastic bracket 21, which is filled in the anti-rotation groove 233; and a first limiting slot 234 and a second limiting slot 235 are formed on opposite sides of the outer surface of the outlet end of the metal head 23 and are oppositely penetrated to the positioning groove 232, and a first limiting block 212 and a second limiting block 213 are formed on the corresponding positions of the plastic bracket 21, which are filled in the first limiting slot 234 and the second limiting slot 235 respectively. The anti-rotation groove 233 of the metal head 23 cooperates with the anti-rotation block 211 on the plastic bracket 21 to restrict the metal head 23 from rotating around an axis of the metal guiding tube 22. The first limiting slot 234 and the second limiting slot 235 of the metal head 23 cooperate with the first limiting block 212 and the second limiting block 213 on the plastic bracket 21 to restrict the metal head 23 from moving along the axis of the metal guiding tube 22 and rotating around the axis of the metal guiding tube 22. At this point, the plastic bracket 21, the metal guiding tube 22, and the metal head 23 can be firmly joined together. It will be apparent to those skilled in the art that in various embodiments of the present application, the plastic bracket 21, the metal guiding tube 22, and the metal head 23 can also be processed separately and then assembled into one body.

As shown in FIG. 2, the plastic bracket 21 is provided with a needle outlet 214 corresponding to the outlet end of the metal guiding tube 22, and an inner surface of the needle outlet 214 is larger than an inner surface of the metal guiding tube 22. Therefore, when the needle 4 is moved to the position of the needle outlet 214, it does not come into contact with the plastic needle outlet 214 of plastic material. Further, as shown in FIG. 2 and FIG. 3, the needle insertion groove 231 of the metal head 23 has a partial bellmouth shape which is open upward, and is docked with the guiding groove 221 to facilitate insertion of the needle 4.

When the ultrasound interventional operation is performed, the endocavity ultrasound probe 1 is externally sheathed with a protective cover 3 to be aseptically isolated, and the needle guide apparatus for endocavity ultrasound intervention 2 is detachably mounted and fixed to the endocavity ultrasound probe 1 through a mounting structure 215 disposed on the plastic bracket 21. The direction of an arrow shown in FIG. 1 is the guiding direction of the interventional operation. The needle 4 first comes into contact with the metal head 23, then passes through the metal guiding tube 22, and finally comes out of the needle outlet 214 of the plastic bracket 21 and begins to enter the surgical target. The needle 4 does not come into contact with the plastic material during the entire process from the needle insertion groove 231 of the metal head 23 into the guiding groove 221 in the metal guiding tube 22 and out of the needle outlet 214 of the plastic bracket 21, thus the case that the needle tip of the needle 4 breaks the plastic material to cause the debris entering the human body is avoided, ensuring safe, reliable and easy operation of the interventional operation.

In a needle guide apparatus for endocavity ultrasound intervention according to another embodiment of the present application, the plastic bracket 21 can be composed of two parts, a needle inlet bracket and a needle outlet bracket, which are detachably mounted with the endocavity ultrasound probe 2, respectively. Both ends of the metal guiding tube 22 are respectively housed in the needle inlet bracket and the needle outlet bracket and an intermediate portion is exposed, and the metal head 23 is disposed on the needle inlet bracket and is docked with the guiding groove 221 of the metal guiding tube 22 in the same manner as the foregoing embodiment. Similarly, the needle outlet bracket may be provided with the needle outlets 214 of the same form as the foregoing embodiment.

The above is only the preferred embodiments of the present application, and is not intended to limit the present application. Any modifications, equivalent substitutions and improvements made within the spirit and principles of the present application should be included within the protection scope of the present application.

The invention claimed is:

1. A needle guide apparatus for endocavity ultrasound intervention, comprising a plastic bracket and a needle guiding passage made of metal that is provided in the plastic bracket, wherein the plastic bracket has a mounting structure that is detachably mounted to an endocavity ultrasound probe, and the needle guiding passage comprises a needle insertion groove provided by a metal head and a guiding groove provided by a metal guiding tube, the metal guiding tube is at least partially housed in the plastic bracket, and at least an inlet end of the metal head is exposed outside the plastic bracket; the plastic bracket is injection molded integrally on the needle guiding passage, and the metal head and the plastic bracket are provided with a limiting structure that cooperates to restrict the metal head from moving along an axis of the metal guiding tube and rotating around the axis of the metal guiding tube.

2. The needle guide apparatus for endocavity ultrasound intervention of claim 1, wherein an outlet end of the metal head and an inlet end of the metal guiding tube are positioned by a positioning structure to dock the needle insertion groove with the guiding groove.

3. The needle guide apparatus for endocavity ultrasound intervention of claim 2, wherein a positioning groove that is matched with the inlet end of the metal guiding tube is provided at the outlet end of the metal head, and the inlet end of the metal guiding tube is inserted in the positioning groove.

4. The needle guide apparatus for endocavity ultrasound intervention of claim 3, wherein the limiting structure comprises an anti-rotation groove formed on an outer surface of the outlet end of the metal head and an anti-rotation block formed on the plastic bracket at a corresponding position to be filled into the anti-rotation groove.

5. The needle guide apparatus for endocavity ultrasound intervention of claim 4, wherein the limiting structure further comprises a first limiting slot and a second limiting slot that are formed on opposite sides of the outer surface of the outlet end of the metal head and are oppositely penetrated to the positioning groove, and a first limiting block and a second limiting block that are formed on the plastic bracket at corresponding positions to be filled into the first limiting slot and the second limiting slot respectively.

6. The needle guide apparatus for endocavity ultrasound intervention of claim 1, wherein the metal guiding tube is a circular tube providing a circular guiding groove, and the needle insertion groove of the metal head has a bellmouth shape or a partial bellmouth shape which is open upward.

7. The needle guide apparatus for endocavity ultrasound intervention of claim 1, wherein the plastic bracket is provided with a needle outlet that is docked with the needle guiding passage, and an inner surface of the needle outlet is larger than an inner surface of the needle guiding passage.

* * * * *